US007910092B2

(12) United States Patent
Carminati et al.

(10) Patent No.: US 7,910,092 B2
(45) Date of Patent: Mar. 22, 2011

(54) USE OF THE LONG PENTRAXIN PTX3 FOR THE PREVENTION OR TREATMENT OF VIRAL DISEASES

(75) Inventors: Paolo Carminati, Milan (IT); Marica Sassano, Caserta (IT); Francesco Bistoni, Perugia (IT); Luigina Romani, Perugia (IT); Silvia Bozza, Corciano (IT)

(73) Assignee: Tecnogen S.p.A., Piana di Monte Verna (IT)

( * ) Notice: Subject to any disclaimer, the term of this patent is extended or adjusted under 35 U.S.C. 154(b) by 0 days.

(21) Appl. No.: 12/162,866

(22) PCT Filed: Feb. 28, 2007

(86) PCT No.: PCT/EP2007/051889
§ 371 (c)(1),
(2), (4) Date: Nov. 24, 2008

(87) PCT Pub. No.: WO2007/104646
PCT Pub. Date: Sep. 20, 2007

(65) Prior Publication Data
US 2009/0286726 A1 Nov. 19, 2009

(30) Foreign Application Priority Data
Mar. 10, 2006 (EP) .................................. 06004971

(51) Int. Cl.
*A61K 35/00* (2006.01)
(52) U.S. Cl. .................... 424/93.1; 424/230.1; 350/350
(58) Field of Classification Search ................. None
See application file for complete search history.

(56) References Cited

U.S. PATENT DOCUMENTS

| 6,001,799 | A | 12/1999 | Chretien et al. |
| 6,872,541 | B2 | 3/2005 | Mills |
| 7,683,032 | B2 | 3/2010 | Carminati et al. |
| 2001/0012830 | A1 | 8/2001 | Horwitz |
| 2004/0023879 | A1 | 2/2004 | Mantovani et al. |
| 2004/0029803 | A1 | 2/2004 | Mantovani et al. |
| 2004/0137544 | A1 | 7/2004 | Latini et al. |
| 2004/0142879 | A1 | 7/2004 | Calvani |
| 2005/0043230 | A1 | 2/2005 | Presta et al. |
| 2006/0286617 | A1 | 12/2006 | Latini et al. |
| 2007/0098722 | A1 | 5/2007 | Bottazzi et al. |
| 2008/0015153 | A1 | 1/2008 | Bottazzi et al. |
| 2008/0026997 | A1 | 1/2008 | Carminati et al. |
| 2009/0275508 | A1 | 11/2009 | Romani et al. |
| 2010/0209442 | A1 | 8/2010 | Carminati et al. |

FOREIGN PATENT DOCUMENTS

| WO | 98/18491 | 5/1998 |
| WO | WO 99/32516 | 7/1999 |
| WO | WO 2006/037744 | 4/2006 |

OTHER PUBLICATIONS

Reading et al., "Antiviral activity of the long chain pentraxin PTX3 against influenza viruses" J. Immunol. 180:3391-3398, 2008.
Mairuhu et al., "Elevated plasma levels of the long pentraxin PTX3, in severe dengue virus infections" J. Med. Virol., 76:547-552, 2005.
Soares et al., "Dual function of the long pentraxin PTX3 in resistance against pulmonary infection with *Klebsiella pneumoniae* in transgenic mice" Microbes and Infection, 8:1321-1329, 2006.
He et al., "Long pentraxin 3 in pulmonary infection and acute lung injury" Am. J. Phisol. Lung Cell. Mol. Physiol., 292: L1039-L1049, 2007.
Gewurz et al., "Structure and function of the pentraxins" Curr. Opin. Immunol., 7:54-64, 1995.
Bottazzi et al. "Multimer formation and ligand recognition by the long pentraxin PTX3. Similarities and differences with the short pentraxins C-reactive protein and serum amyloid P component" J. Biol. Chem. 272:32817-32823 (1997).
Introna et al. "Cloning of mouse PTX3 a new member of the pentraxin gene family expressed at extrahepatic sites." Blood 87:1862-1872 (1996).
Nauta, A. "Biochemical and Function Characterization of the Interaction . . . " Eur. J. Immunol., vol. 33, pp. 465-473, 2003.
Siripont, J. et al. "Receptor-Mediated Binding of the Acute-Phase . . . ", Cellular Immunology, vol. 117, pp. 239-252, 1988.
Tennent, G. et al. "Glycobiology of the Pentraxins", Biochemical Society Transactions, vol. 22, No. 1, pp. 74-79, 1994.
Camozzi et al., Arterioscler Thromb Vasc Biol. Sep. 2005;25(9):1837-42. Epub Jul. 14, 2005.
Souza et al., Am J Pathol. Apr. 2009;174(4):1309-18. Epub Mar. 12, 2009.
Bassi et al., Clin Rev Allergy Immunol. Nov. 18, 2008. [Epub ahead of print], 8 pages.
Bevelacqua et al., Int J Mol Med. Sep. 2006;18(3):415-23.
Kataoka et al., Atherosclerosis. Mar. 2008;197(1):368-74. Epub Jul. 19, 2007.
Luchetti et al., Clin Exp Immunol2000, 119:196-202.
Rolph et al., Arterioscler Thomb Vasc Bioi 2002, 22: 1-5.
Polentarutti et al., "Interferon-Gamma Inhibits Expression of the Long Pentraxin PTX3 in Rheumatoid Arthritis (RA)" European J, Immunol., vol. 28, 1998, pp. 496-501.
Mocarski et al., Pro Natl. Acad. Sci. USA vol. 90, pp. 104-108, 1993.

*Primary Examiner* — Bao Li
(74) *Attorney, Agent, or Firm* — Lucas & Mercanti, LLP (57) ABSTRACT

It is described the use of the long pentraxin PTX3 (PTX3) or one of its functional derivatives, for the preparation of a medicament for the prevention or treatment of viral diseases and/or for inhibiting virus activation.

2 Claims, 6 Drawing Sheets

SEQUENCE LISTING

```
<160> NUMBER OF SEQ ID NOS: 4

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aagcagcaca tccgcaccct gagcgcc                                            27

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 2
ccaggcgctc ccggcggccc gctctcg                                          27

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gagaccttca acaccccagc c                                                21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ggccatctct tgctcgaagt c                                                21
```

USE OF THE LONG PENTRAXIN PTX3 FOR THE PREVENTION OR TREATMENT OF VIRAL DISEASES

The invention described herein relates to the use of long pentraxin PTX3 (PTX3) or one of its functional derivatives, for the preparation of a medicament for the prevention or treatment of viral diseases and/or for inhibiting virus activation, in which said virus is selected from the group consisting of herpes virus, such as cytomegalovirus (CMV); influenza virus, such as H1N1, H3N2, H5N1 or H5N7 virus; paramixovirus, such as measles; respiratory syncytial virus; coronavirus, such as SARS; HIV Virus; hepatitis virus; or rotavirus.

Human cytomegalovirus (HCMV) is a herpesvirus commonly found in about 50% of the general population. About 90% of people with HIV carry HCMV. In the general population, the virus usually remains latent in the tissues of the body after the initial infection. It can, however, be shed in the mouth, urine, and genital tract, serving as a source of infection for other people. Infection with HCMV can result in secondary, more severe infections if the immune system becomes compromised for any reason.

Roughly 5% of infants who get HCMV through vertical transmission have serious birth defects. These can include brain damage, growth failure, blindness, and other defects. This problem usually occurs when the mother becomes infected with HCMV for the first time during pregnancy.

In the general adult population, HCMV lies dormant, but may be associated with the development of coronary artery disease. Infection with HCMV has been associated with the development of arterial plaques and atherosclerosis.

HCMV can cause serious problems in people with weakened immune systems.

This is most commonly a problem in people with AIDS or in those patients on immunosuppressive therapy. HCMV infects between 75 and 100% of HIV positive patients. The most common complications associated with HCMV include chorioretinitis; gastrointestinal tract infections, including hepatitis, esophagitis, colitis, gastritis, and pancreatitis; neurologic involvement, including encephalitis and polyradiculitis; pulmonary involvement; and epididymitis.

People with widespread cancer or people who receive organ or bone marrow transplants are commonly affected. Infection may be due to a first time exposure to HCMV or as a result of reactivated HCMV. In transplant and cancer patients, HCMV usually causes pneumonia or a gastrointestinal infection resulting in diarrhea, which may cause death. Furthermore, HCMV contributes to the development of chronic allograft dysfunction in solid organ transplant recipients. The relationship between HCMV disease and the development of bronchiolitis obliterans in lung transplant recipients is well established. Additionally, HCMV is one of a number of risk factors that may lead to allograft injury. Direct viral invasion of the allograph may cause HCMV hepatitis in liver or kidney transplant patients. In addition to direct syndromes produced by HCMV, infection with this virus may increase the risk for fungal and other opportunistic infections, such as *Pneumocystis carinii* pneumonia and Epstein-Barr virus-related post transplant lymphoproliferative disease.

Most people have been infected with HCMV by the time they are adults. Anyone receiving a blood transfusion or an organ transplant is at risk for a HCMV infection.

Furthermore, people with weakened immune systems and unborn children are at risk for severe disease.

Treating active HCMV in people with weakened immune systems is currently done with antiviral agents, such as ganciclovir, foscarnet, and cidofovir.

Influenza viruses causes flu, a contagious disease that infect the respiratory tract (nose, throat, and lungs) in humans. Influenza usually comes on suddenly and may include these symptoms: fever, headache, malaise (a feeling of being ill and without energy that can be extreme), cough, sore throat, nasal congestion and body aches.

Paramyxoviridae viruses induce a wide range of distinct clinical illnesses in humans, these include measles virus; mumps virus, which has symptoms of parotitis, orchitis and encephalitis; and the parainfluenza viruses which are respiratory pathogens.

Respiratory syncytial virus (RSV) is the most common cause of bronchiolitis and pneumonia among infants and children under 1 year of age. Illness begins most frequently with fever, runny nose, cough, and sometimes wheezing. RSV also causes repeated infections throughout life, usually associated with moderate-to-severe cold-like symptoms; however, severe lower respiratory tract disease may occur at any age, especially among the elderly or among those with compromised cardiac, pulmonary, or immune systems.

Coronaviruses infect a variety of mammals and birds, in humans they cause respiratory infections including Severe Acute Respiratory Syndrome (SARS) Enteric infections and Neurological syndromes. Adult infections are less common and re-infections appear to occur throughout life.

The Human Immunodeficiency Virus (HIV) is a retrovirus. The genetic information in a retrovirus particle is encoded by RNA. Upon entry into the host cell this RNA is copied into DNA by the virus enzyme reverse transcriptase. This cDNA copy of the virus' genetic information can integrate into the host cell chromosomes in the nucleus. This provirus can lay dormant for many cell divisions before being reactivated and producing more infectious retrovirus particles.

Viral hepatitis is any type of liver inflammation caused by a viral infection. The three most common viruses now recognized to cause liver disease are hepatitis A, hepatitis B, and hepatitis non-A, non-B (also called hepatitis C). Several other types have been recognized: hepatitis D, hepatitis E, and the recently identified hepatitis G. A seventh type (hepatitis F) is suspected but not yet confirmed.

Rotavirus is the most common cause of severe diarrhea among children, resulting in the hospitalization of approximately 55,000 children each year in the United States and the death of over 600,000 children annually worldwide.

PTX3 is a protein expressed in various cell types (Bottazzi, et al., J. Biol. Chem, 1997; 272; 32817-32823), particularly in mononuclear phagocytes and endothelial cells after exposure to the inflammatory cytokines Interleukin1beta (IL-1beta) and Tumor Necrosis Factor alpha (TNF-alpha).

This protein consists of two structural domains, an N-terminal unrelated to any known molecule, and a C-terminal similar to the short pentraxins such as C-reactive protein (CRP). A substantial similarity has been found between human PTXS (hPTX3) and animal PTX3s.

The PTX3 gene is located on mouse chromosome 3, in a region similar to the human 3q region (q24-28), in keeping with the documented location of hPTX3 in the 3q 25 region. Moreover, mouse PTX3 (mPTX3) (Introna, M., et al.: Blood, 87 (1996); 1862-1872) is very similar to hPTX3 on the basis of organisation, location and sequence (Breviario, F., et al.: J. Biol. Chem., 267. 22190, 1992).

In particular, the degree of identity between the sequences is 82% between the human gene and the mouse gene, and reaches 92% if conservative substitutions are considered.

The high degree of similarity between the sequence of hPTX3 and that of mPTX3 is a sign of the high degree of conservation of pentraxin in the course of evolution (Adv. Immunol. 34: 141, 1983).

For an overview of the pentraxins, see H. Gewurz, et al., Current Opinion in Immunology, 1995, 7.54-64.

Previous uses of PTX3 are already known.

The international patent application WO99/32516 (which is the closest prior art) filed in the name of the present applicant, describes the use of long pentraxin PTX3 for the therapy of infectious (fungi, bacteria, protozoa or viruses), inflammatory or tumoral diseases. In WO99/32516 it is never mentioned that PTX3 would have been useful for treating HCMV or influenza viruses.

WO02/38169 describes the use of long pentraxin PTX3 for the preparation of a medicament useful for the treatment of diseases associated with abnormal activation of growth factor FGF-2.

WO02/36151 describes the use of long pentraxin PTX3 for the treatment of autoimmune diseases.

WO03/011326 describes the use of long pentraxin PTX3 for the treatment of female infertility.

WO03/084561 describes the use of long pentraxin PTX3 for the preparation of a medicament for the treatment of tumoral diseases associated with abnormal activation of growth factor FGF-8.

WO03072603 describes the use of the long pentraxin PTX3 for preparing an autologous vaccine for the treatment of tumours.

WO2005060988 describes the use of pentraxin PTX3 and of its combination with TSG-6 for the preparation of a medicament for the treatment of bone or cartilage diseases and for the treatment of female infertility.

WO2005060997 describes the use of inhibitors of long pentraxin PTX3 for the preparation of a medicament for the prevention and treatment of autoimmune diseases and of degenerative diseases of bone and cartilage.

WO2005107791 describes the combination of pentraxin PTX3 with antifungals for the treatment of fungal infections and particularly for infections caused by *Aspergillus fumigatus*.

Blood, 1 Jan. 2006, Volume 107, Number 1, describes that PTX3 contributes to limit tissue damage under inflammatory conditions and the activations of autoreactive cells.

Surprisingly and unexpectedly, it has now been found that the long pentraxin PTX3 is useful for the preparation of a medicament for the inhibition of the virus activation and/or for the prevention or treatment of viral diseases.

It is therefore an object of the present invention the use of an effective amount of the long pentraxin PTX3, for preparing a medicament for the inhibition of the activation of virus diseases selected from the group comprising herpes virus, such as cytomegalovirus (CMV); influenza virus, such as H1N1, H3N2, H5N1 or H5N7 virus; paramixovirus, such as measles; respiratory syncytial virus; coronavirus, such as SARS: HIV Virus; hepatitis virus; or rotavirus disease; in a mammal subject.

It is a further object of the present invention the use of an effective amount of the long pentraxin PTX3 for preparing a medicament for the prevention and/or treatment of virus diseases selected from the group comprising herpes virus, such as cytomegalovirus (CMV); influenza virus, such as H1N1, H3N2, H5N1 or H5N7 virus, paramixovirus, such as measles, respiratory syncytial virus; coronavirus, such as SARS, HIV Virus; hepatitis virus, or rotavirus; in a mammal subject.

It is a further object of the present invention the use of an effective amount of the long pentraxin PTX3 for preparing a medicament for treating a cytomegalovirus induced syndrome, in which;
said syndrome is CMV mononucleosis;
said syndrome is associated with an immunocompromised host;
said immunocompromised host has AIDS;
said immunocompromised host is an organ transplant recipient.

It is a further object of the present invention the use of an effective amount of the long pentraxin PTX3 for preparing a medicament for treating the influenza induced syndrome, in which said syndrome is due to a virus selected from the group consisting of H1N1, H3N2, H5N1 or H5N7 virus.

The following non limiting examples illustrate the invention.

Materials and Methods

Abbreviations Used:

HCMV: human CMV; MCMV: murine CMV; DC: dendritic cell; gB: glycoprotein B; pDC: plasmacytoid DC; PTX3: pentraxin 3.

Mice

Female 8 to 12-wk old wild-type (WT) inbred C57BL6, 129/Sv and BALB/c mice were purchased from Charles River Breeding Laboratories (Calco, Italy). Breeding pairs of homozygous TLR9-(TLR9$^{-/-}$), TLR4-(TLR4$^{-/-}$), TLR2-(TLR2$^{-/-}$), MyD88-(MyD88$^{-/-}$) and IL-12 p40 (IL-12p40$^{-/-}$)-deficient mice (all on the C57BL6 background), and IFN-γ-deficient mice (IFN-γ$^{-/-}$) (on the BALB/c background), (Science 2003, 301:640) (Nature Immunol. 2001, 2:1144) (Proc. Natl. Acad. Sci. U.S.A. 2004, 101:3516) (Immunity 2004, 21:107) (J. Exp. Med. 2002, 195:517). PTX3-deficient mice (PTX3$^{-/-}$) (on 129/Sv-C57BL6 mixed background generated) (Nature 2002, 420:182). Mice deficient for the IFN-αβ receptor (IFN-αβR$^{-/-}$) were used (J. Exp. Med. 2003, 197:885).

Pathogens, Infections and Treatments

Stocks of Smith strain MCMV salivary gland extracts were prepared from BALB/c mice and titered in a standard plaque assay on BALB/c murine embryonic fibroblast (MEF) cells (J. Gen. Virol. 2002, 83:2983).

The influenza virus A/Sydney/5/97 (H3N2) strain was grown in embrionated eggs and titered in a standar plaque assay on Madin Darby Canine Kidney (MDCK) (Virology 2005, 340:296).

Infections were initiated by intraperitoneally injection of $10^5$ (BALB/c), $5 \times 10^5$ (C57BL6, PTX3$^{+/+}$ and PTX3$^{-/-}$) plaque forming units (PFU) of MCMV. Removed tissues were individually homogenized, supernatants stored at −80° C., and virus titers were subsequently quantified on MEF by standard plaque assay. PTX3 was obtained under endotoxin-free conditions by immunoaffinity of culture supernatants of CHO cells transfected with PTX3 (Nature 2002, 420:182) and administered intraperitoneally (1 or 4 mg/kg) for 7 or 14 days beginning the day of the infection. Gancyclovir (GCV) (Cymevene; from Recordati, Milan, Italy) was administered at 40 mg/kg intraperitoneally, three times a week, beginning 6 hours after infection. Controls received the diluent alone. For histology, sections of paraffin-embedded tissues were stained with the periodic acid-Schiff procedure. The strain of *A. fumigatus* and the culture conditions were as described (Blood 2003, 102:3807).

For co-infection, MCMV-infected mice received $5 \times 10^5$ *Aspergillus conidia* intravenously, 2 weeks after the viral infection and subsequent treatment with PTX3 (1 mg/kg/ intraperitoneally) daily for a week. Quantification of fungal growth was done by the chitin assay and results are expressed as micrograms of glucosamine/organ (Blood 2003, 102:3807).

Experimental HSCT Model

Recipient mice were exposed to a lethal dose of 8 Gy and infused with $10^7$/mL of T cell-depleted donor cells (<1% of contaminating T-cells) from donor allogeneic mice, as described (Blood 2003, 102:3807).

MCMV Reactivation Following HSCT

Mice were infected with MCMV as above. Three months later, MCMV latency was confirmed by the absence of acute MCMV infection in spleen (J Immunol 2005, 174:1587) and lung (J Virol 1997, 71:2980), both organs considered primary sites of molecular MCMV latency. Infected mice were used either as recipients of allogeneic donor uninfected bone marrow cells ($MCMV^+$ recipients) or as donors of bone marrow cells ($MCMV^+$ donors) to be injected into uninfected recipients. PTX3 (1 mg/kg/intraperitoneally) was given daily for 2 weeks, starting the day after HSCT. Dying or surviving mice (sacrificed thirty days after HSCT) were assessed for MCMV viral loads in the lungs by the plaque assay.

DC Subset Generation

Murine DC were obtained from bone marrow cells cultured in Iscove's modified medium (Blood 2003, 102:3807) in the presence of 150 U/mL mouse rGM-CSF (Sigma) and 75 U/mL rIL-4) (R&D Systems) for 7 days to obtain $CD11^+DC$ or 200 ng/mL FLT3-L (Immunex Corporation, Seattle, Wash.) for 9 days to obtain pDC (Blood 2003, 102:3807). Final maturation was done as described in Blood 2003, 102: 3807, $CD11^+DC$ were discriminated on $CD11c^{high}$ expression and were distinctly composed of $CD8\alpha^+$ DC and $CD11b^+$ DC. pDC were defined as $CD11c^{low}$, $Ly6G^+$ $CD8\alpha^{+/-}$ cells. Spleen DC were purified by magnetic-activated sorting using CD11c MicroBeads and MidiMacs (Miltenyi Biotec). Photographs were taken using a high Resolution Microscopy Colour Camera AxioCam, using the AxioVision Software Rel. 3.1 (Carl Zeiss S.p.A., Milano, Italy).

Flow Cytometry Analyses

For all FACS analyses, cells were first incubated with anti-CD16/32 (2.4G2) to ensure blocking of FcRs and analyzed for antigen expression with a FACScan flow cytofluorometer (Becton Dickinson, Mountain View, Calif.) equipped with CELLQuest™ software. Control staining of cells with irrelevant Ab was used to obtain background fluorescence values. Abs were from BD Pharmingen. The data obtained were evaluated as percentage of positive cells. Histograms are representative of one out of four independent experiments.

Plague Assay

Plaques assay was determined on cells grown to subconfluence and incubated with serially diluted virus samples for 2 hours at 37° C. (Science 2001, 292:934).

All organs from uninfected animals were negative viruses. Virus titers are expressed as $log_{10}$ (mean±standard errors, SE).

PTX3 Binding Assays to Immobilized Viruses

The 96-well plates were coated overnight at 4° C.° with a 0.05 M carbonate solution (0.159 g of $Na_2CO_3$ and 0.293 g of $NaHCO_3$, pH 9.8) (Sigma) containing the $10^4$ PFU MCMV or H3N2 human influenza viruses. Non-specific binding sites were blocked by 5% bovine serum albumin in PBS. PTX3 binding to HCMV was measured using HCMV Ag-coated plates (AID GmbH, Germany). Binding was performed using 0.5, 1 or 5 µg/mL biotin-labelled PTX3 ($PTX3bio^+$) for 2 hours at 37° C. Inhibition was performed by pre-incubation with 0.5 or 5 µg/mL unbiotinilated PTX3 ($PTX3bio^-$) for 2 hours at 37° C. prior the addition of $PTX3bio^+$. The optical density at 450 nm was read using the Horseradish Peroxidase Substrate Kit (Bio-Rad Laboratories, Life Science Group, Segrate Italy). Non-specific binding of PTX3 to virus-uncoated plates was minimal.

Inhibition of Viral Replication

MEF cells ($2\times10^4$/well) grown to subconfluence were either pre-incubated for 2 hours at 37° C. with 5-0.5 µg/mL PTX3 diluted in serum-free DMEM and then added of $10^4$ PFU MCMV or left untreated and infected with $10^4$ PFU MCMV pre-treated with 5-0.5 µg/mL PTX3 for 2 hours at 37° C. In selected experiments, a PTX3 neutralizing monoclonal antibody (70 ng/100 µL) (Clin. Exp. Immunol. 2000, 119-196) was used to minimize carry over effects-Infectivity was measured after 72 hours incubation at 37° C., as indicated by initial experiments. One well per plate was mock infected and served as a cell control. In the case of DC, $10^6$/cell/well were either pre-incubated for 2 hours at 37° C. with 5 µg/mL PTX3 diluted in serum-free DMEM and then added of $10^5$ PFU MCMV or were untreated and infected with $10^5$ PFU MCMV pre-treated with 5 µg/mL PTX3 for 2 hours at 37° C. Cells were assayed for infectivity after 48 hours of incubation. For inhibition of H3N2 replication, $3\times10^4$ PFU virions were exposed to 5-0.5 µg/mL PTX3 for 2 hours at 37° C. before addition to confluent MDCK cells. Infectivity was assessed at different days after the infection by plaque assay.

NK Cell Cytotoxic Activity

NK cells, purified from spleens by DX5 microbeads (Miltenyi Biotec), were defined as $NK1.1^+CD3^-$ cells. NK cytolytic activity was assessed against $^{51}Cr$-labeled YAC-1 lymphoma cells (Blood 2005, 106:4397).

Real-Time RT-PCR for Quantification of MCMV mRNA

A highly sensitive RT-PCR assay was used for amplification of the 356-bp segment of MCMV glycoprotein B (gB) DNA (Virus Res 2003, 98:17).

Total cellular RNA was obtained by TRIzol extraction after cells disruption in liquid nitrogen (Invitrogen Life Technologies, Milan, Italy). Synthesis and PCR of cDNA were done as described (Blood 2003, 102:3807). Synthetic DNA ologonucleotide primers were selected from the published sequence of the MCMV gB gene (J. Immunol. 2005, 175: 6723).

The sense primers was based on the cDNA No. 2416-2443: 5'-AAG-CAG-CAC-ATC-CGC-ACC-CTG-AGC-GCC-3' (SEQ ID NO: 1), and the antisense on No. 2745-2772: 5'-CCA-GGC-GCT-CCC-GGC-GGC-CCG-CTC-TCG-3' (SEQ ID NO: 2). To verify the presence of DNA in each experiment, parallel actin amplification was performed using the following oligonucleotides: 5'-GAG-ACC-TTC-AAC-ACC-CCA-GCC (sense) (SEQ ID NO: 3) and 5'-GGC-CAT-CTC-TTG-CTC-GAA-GTC (anti-sense) (SEQ ID NO: 4). The PCR was performed in a thermal cycle (MasterCycler gradient; Eppendorf), cycling conditions were initial denaturation for 3 min at 95° C., followed by cycles of 1 min at 95° C., 1 min at 50° C., and 20 s at 72° C., and a final extension for 10 min at 72° C.

Quantification of Cytokines by ELISA and ELISPOT Assays

The levels of cytokines in the culture supernatants of mitogen-stimulated spleen cells (48 hours stimulation with 10 µg/mL ConA) or MCMV-pulsed DC (24 hours) were determined by ELISA (R&D Systems and PBL, Biomedical Lab, Milan, Italy). The detection limits (pg/mL) of the assays were <16 for IL-12 p70, <10 for IFN-γ, <3 for IL-10 and <10 for IFN-α. IFN-γ-producing NK cells were enumerated by ELISPOT assay on purified NK from spleens as described (Blood 2003, 102:3807). Results are expressed as the mean number of cytokine-producing cells (±SE) per $10^5$ cells, calculated using replicates of serial 2-fold dilutions of cells.

Quantification of PTX3 by ELISA

Quantification of PTX3 in sera and lung homogenates (a week after the infection) was done by ELISA as described (Eur. J. Immunol. 2003, 33:2886).

Statistical Analyses

Student's paired t test was used to determine the significance of values in experimental groups (significance was defined as P<0.05). Survival data were analyzed using the Mann-Whitney U test. In vivo groups consisted of 6 animals. Unless otherwise indicated, data are mean±SE.

Results

PTX3 Inhibits CMV Infection In Vitro

Figure 1:
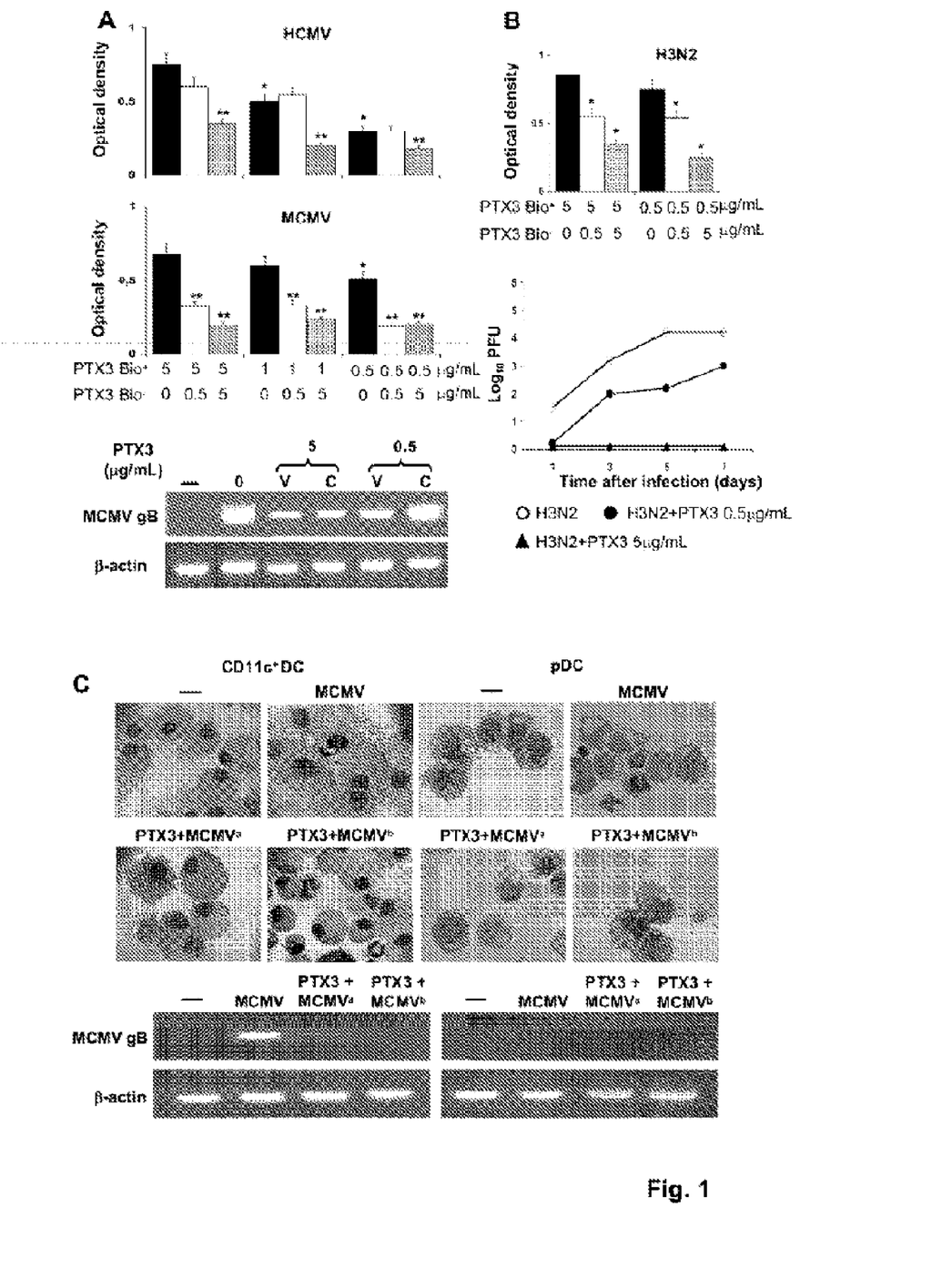

To test whether PTX3 affects CMV infection in vitro, was evaluated i) the ability of PTX3 to bind to HCMV or MCMV, ii) the effects of virus exposure to PTX3 on productive infection into permissive MEF cells and iii) the effects of MEF cell treatment with PTX3 on subsequent viral infection. PTX3 bound both HMCV and MCMV in a dose-dependent manner and the binding was significantly reduced in the presence of unlabeled PTX3 (FIG. 1A). The binding of PTX3 to HCMV was not inhibited in the presence of human antibodies directed against the 150 (late), 65 and 52 (early) or 28 (specific) kDa antigens, a finding suggesting the diversity of viral molecules recognized by PTX3 and human specific antibodies. Exposure to PTX3 strongly inhibited, in a dose-dependent manner, viral infection, as assessed 72 hours later by the reduced levels of MCMV gB transcript in infected cells (FIG. 1A). The inhibitory effect was rapid and inactivation was obtained already after 30-45 minutes of exposure. Interestingly, pre-treatment of cells with the highest concentration of PTX3 also inhibited the infection. Because experiments in which residual PTX3 was neutralized by specific antibodies ruled out the possible carry over effects of free PTX3 on either cells or the virus, these findings suggest that PTX3 affects viral infectivity and the permissivity of cells to the infection. To evaluate whether PTX3 would similarly bind other enveloped viruses, was assessed the ability of PTX3 to bind the H3N2 human influenza virus and inhibit the infectivity in vitro. FIG. 1B shows that PTX3 strongly bound the virus in a concentration and specific manner and greatly inhibited its infectivity in vitro, as determined by the complete reduced cytopathic effect observed at the highest concentration of PTX3 used PTX3 also slightly delayed the infection upon pretreatment of cells, a finding confirming a possible effect of PTX3 on cell permissivity to the infection. In both types of cells, PTX3 had no visible effect on the confluency of the cell monolayer and/or cell morphology, confirming that PTX3 is nontoxic.

Acute infection with MCMV induces a transient, but profound immunosuppression in susceptible BALB/c mice, which can be linked to infection of CD11$^+$DC (Nat Immunol 2001, 2:1077). CD11$^+$DC support productive infection of MCMV both in vitro and in vivo, whereas MCMV does not replicate in pDC (J. Exp. Med. 2002, 195:517).

To assess whether PTX3 would also affect MCMV infection of DC, PTX3-treated MCMV was added to CD11$^+$DC and pDC from BALB/c mice and infectivity assessed as above. DC were also pretreated with PTX3 before infection. The results showed that MCMV replicates in CD11$^+$DC but PTX3 treatment of either the virus or the cells greatly reduced viral replication. No viral replication whatsoever could be revealed in pDC (FIG. 1C). PTX3 also reduced viral replication in CD11$^+$DC from C57BL6 mice. These results suggest that PTX3 may prevent MCMV infection by inhibiting viral infectivity and by curtailing the subsequent stages of the infection.

PTX3 Protects from CMV Infection and Reactivation In Vivo

Figure 2:
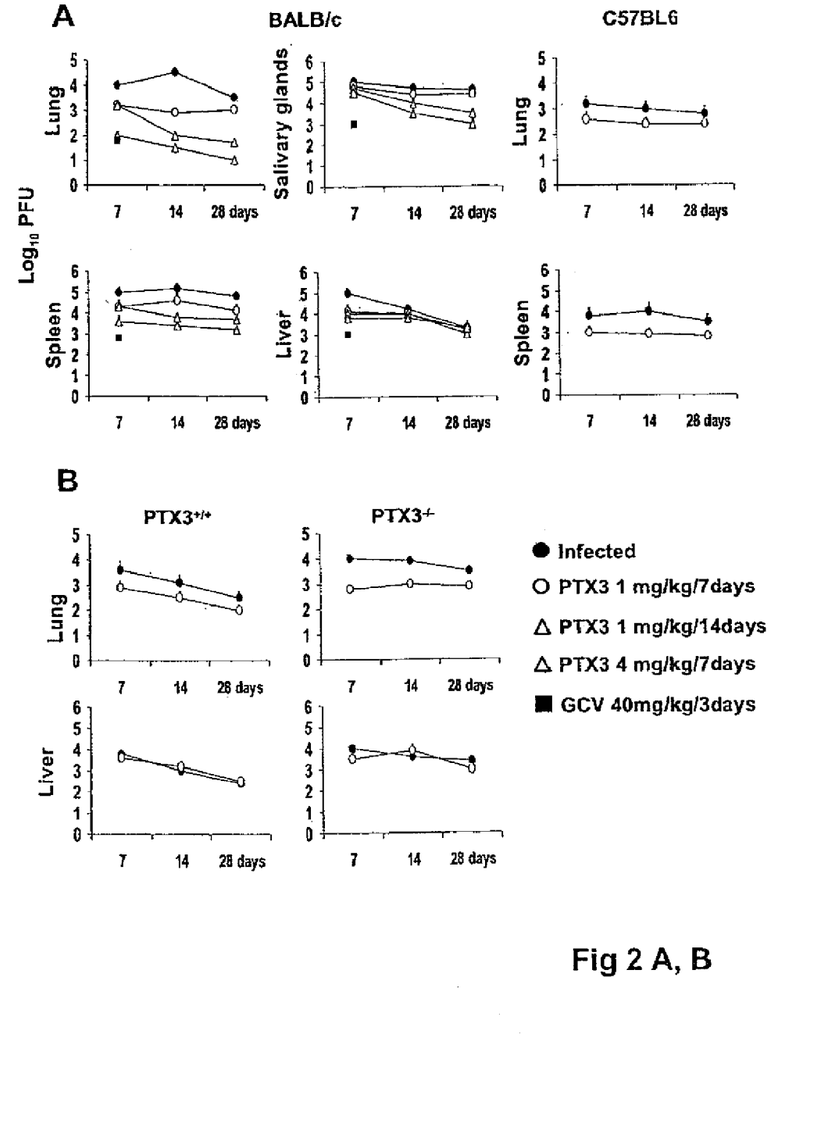

The above results would predict that PTX3 may have antiviral effects in vivo. The effects of PTX3 administration in the acute primary infection of either susceptible (BALB/c) or resistant (C57BL6) mice as well as in reactivation in an experimental model of HSCT was assessed. Mice were infected intraperitoneally with a sub-lethal dose of MCMV, treated with different doses of PTX3 or GCV and the titer loads in spleen, lung, liver and salivary glands were determined at 1, 2 and 4 weeks after the infection by standard plaque assay titration (FIG. 2A). In line with previous reports (Virus Res 2003, 98:17), MCMV replicated to high titers in the visceral organs of susceptible BALB/c than C57BL6 mice, particularly in the early phase of the infection. PTX3, however, significantly decreased the viral load in this early phase, particularly ill the lung and spleen where the effect was similar to that of GCV a week after the infection. The antiviral effect was more pronounced in the lung and spleen of susceptible (more than two logs differences) than resistance mice. The viral titer was lower in the liver of C57BL6 resistant than susceptible BALB/c mice and was almost unaffected by PTX3 treatment. Prolonged treatment (two weeks) with PTX3 was more effective, particularly in the lung and spleen (FIG. 2A). Treatment with PTX3 also ameliorated inflammatory pathology and cellular recruitment in lung, spleen and liver of susceptible mice. These results suggest that PTX3 could be an important component of the host antiviral immune response. To directly address this issue, were measured levels of PTX3 produced during infection and assessed the susceptibility of PTX3$^{-/-}$ mice to MCMV as well as the responsiveness to exogenous PTX3 administration. Circulating levels of PTX3 were not increased after the infection (from 16.0 to 16.7 ng/mL in BALB/c and from 14.0 to 16.0 ng/mL in C57BL6 mice). However, local levels in the lung were significantly increased, particularly in BALB/c mice (from 0.5 to 2.13 ng/mL). Consistent with these findings, PTX3$^{-/-}$ were more susceptible to infection than PTX3$^{+/+}$ mice particularly in the lung whose viral titre was greatly reduced upon treatment with PTX3. PTX3 did not modify the low viral titre in the liver of PTX3$^{-/-}$ mice (FIG. 2B). Interestingly, PTX3 greatly reduced the viral load in the salivary glands of these mice. Histological examination of lung of infected mice revealed a more severe inflammatory pathology in PTX3$^{-/-}$ than PTX3$^{+/+}$ mice, consisting of heavy cellular recruitment associated with signs of parenchimal destruction, peribrochial fibrosis and Globet cell hyperplasia. In both types of mice, however, treatment with PTX3 greatly ameliorated the inflammatory response (FIG. 2C). Together, these data suggest that PTX3 contributes to host immune response to MCMV and that exogenous supply of PTX3 may have decisive antiviral effects.

As reactivation of latent HCMV following allogeneic transplantation is a major clinical problem, the effect of PTX3 was also assessed in MCMV reactivation in experimental HSCT. As HCMV seropositivity of either donor or recipient could be associated with an increased risk of immune-mediated complications (Lancet 2004, Infect Dis. 4:725) the activity of PTX3 was assessed in either MCMV$^+$ recipients or MCMV$^+$ donors, using either susceptible or resistant mice. In each combination, MCMV reactivation occurred within 10 to 20 days after engraftment, as revealed by the decreased survival and the elevated viral replication in the lung. Treatment with PTX3, however, completely prevented viral reactivation, as revealed by long-term survival and almost absent viral replication (FIG. 2D).

PTX3 Protects MCMV-Infected Mice from Invasive Pulmonary Aspergillosis

HCMV reactivation predisposes to severe complications, including superinfection by *Aspergillus* spp. (Oncology (Williston Park) 2000, 14:1701).

As already shown, PTX3 plays a non-redundant role in host antifungal immunity and that PTX3 treatment prevented aspergillosis in experimental HSCT (Nature 2002, 420:182). To assess whether treatment of MCMV-infected mice with PTX3 also decreases the risk of invasive aspergillosis, MCMV-infected mice were treated with PTX3 for a week and infected with *Aspergillus conidia* intratracheally a week later. The results showed that pre-infection with MCMV increased fungal infectivity, as revealed the increased fungal burden in target organs. PTX3-treatment, however, almost completely reduced fungal growth and restored anti-fungal resistance (FIG. 2E).

PTX3 Recovers DC/NK Reactivity and Promotes Cytokine Production in MCMV Infection One of the most striking features of MCMV infection of susceptible BALB/c mice is the early disappearance of CD8$\alpha^+$DC from the spleen, likely due to the lack of NK cells supporting this DC subset (Nat. Immunol. 2001, 2:1077; Nat. Immunol. 2003, 4:175).

The expansion of both CD8$\alpha^+$DC and Ly49H NK cell populations are indeed reciprocally regulated in infection (Mol. Immunol. 2005, 42:547).

Figure 3:
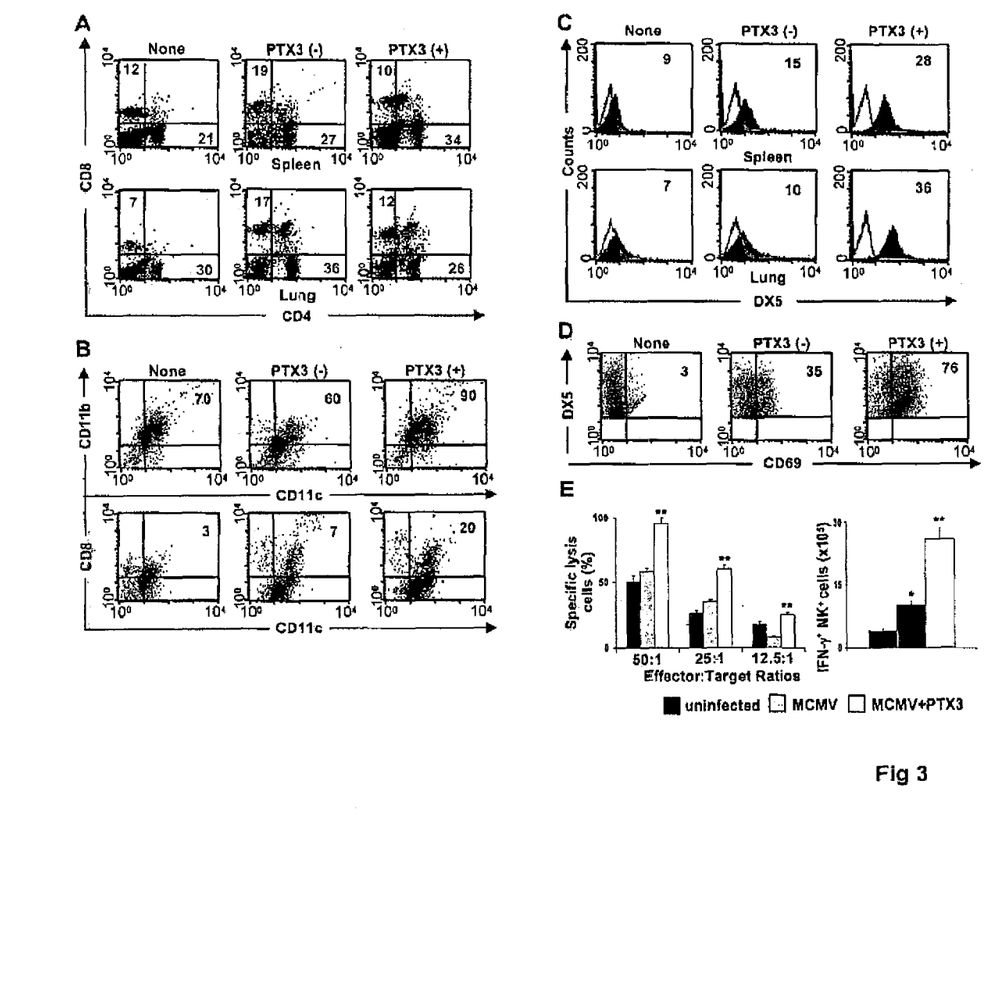

We looked therefore for the effect of PTX3 on the expansion and functional activity of DC subsets and NK cells in the spleen and lung of MCMV-infected mice. FIG. 3 shows that PTX3 treatment, while not affecting the expansion of CD4$^+$ or CD8$^+$ T cells in both organs (A), expanded CD11c$^+$DC and CD8$\alpha^+$DC subsets in the spleen (B), and NK1.1$^+$NK cells in both spleen and lung (C). NK cells were fully activated as revealed by the increased expression of the activation marker CD69 (D). The frequency of IFN-$\gamma$-producing cells and cytotoxic activity of ex-vivo purified splenic NK cells were both significantly up-regulated upon PTX3 treatment (FIG. 3E). PTX3 treatment failed to expand and activate NK cells in uninfected mice.

Figure 4:
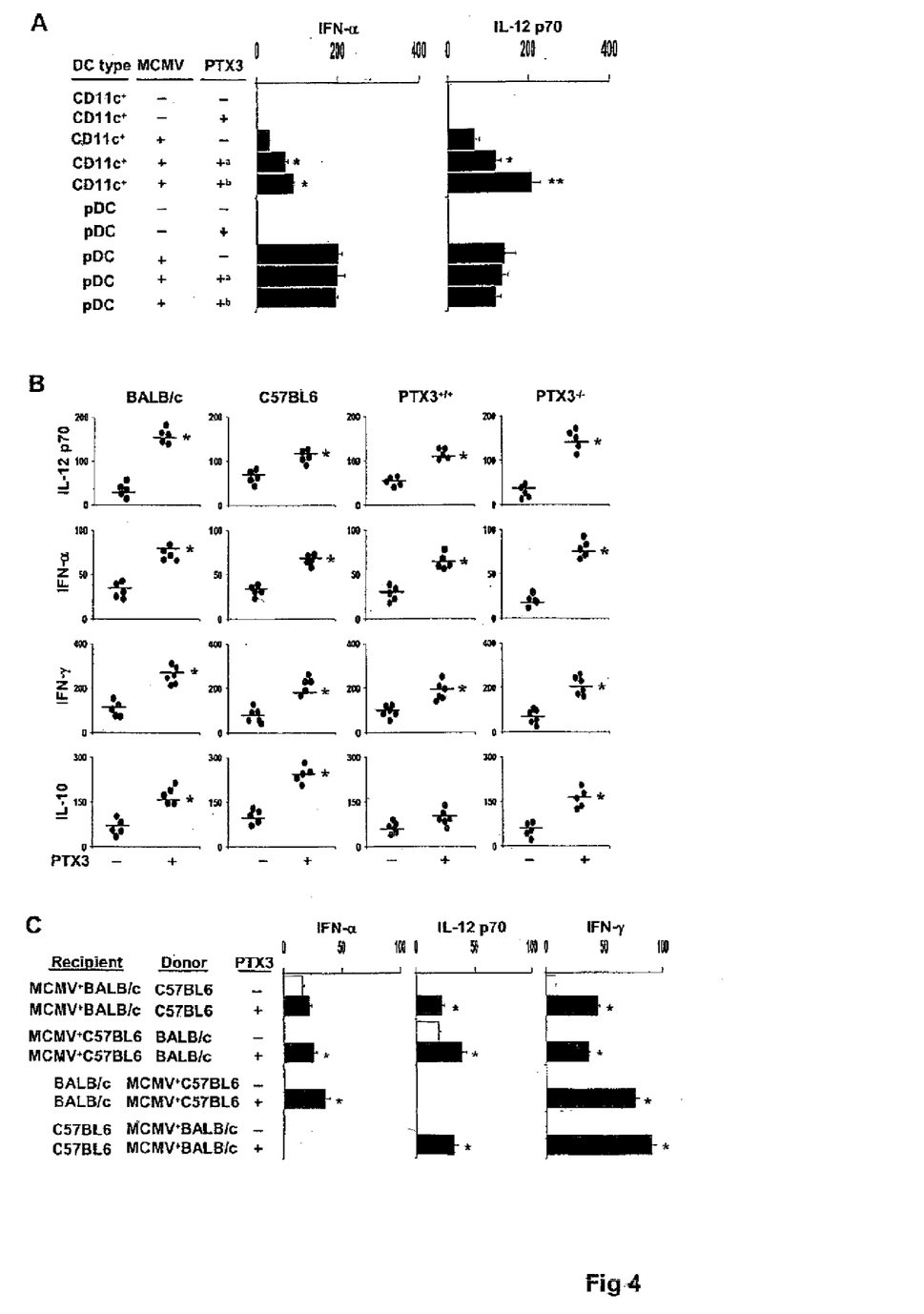

As early activation of NK cells in MCMV infection is mediated by IFN-$\alpha/\beta$ which promotes cytotoxicity and proliferation of NK cells, and IL-12 which induces IFN-$\gamma$ production (J. Exp. Med. 2003, 197:885), was evaluated the pattern of cytokine production by DC subsets exposed to MCMV in the presence of PTX3. Was resorted to bone marrow-derived CD11$^+$DC and pDC subsets from uninfected BALB/c mice to allow to distinguish the effect of PTX3 on DC from that on the virus itself. DC were either pre-treated with PTX3 before viral infection or untreated and infected with PTX3-treated MCMV. In line with previous findings (Nat. Immunol. 2005, 1011), both DC subsets produced IFN-$\alpha$ and IL-12p70 in response to the virus, although pDC more than CD11$^+$DC. PTX3 increased both cytokine productions, but particularly IL-12p70, either after cell or viral treatment but only on CD11c$^+$DC (FIG. 4A) and were induced, although to a lesser extent, with DC from C57BL6 mice. These data, together with those of FIG. 1, indicate that PTX3 neither affects infectivity nor the activation program of pDC in response to MCMV, as opposed to CD11$^+$DC whose infectivity and cytokine production were greatly affected by PTX3.

To correlate the pattern of cytokine production in vitro with that occurring in vivo, was measured IL-12p70, IFN-$\alpha$, IFN-$\gamma$ and IL-10 production in culture supernatants of spleen cells from mice with primary MCMV infection and treated with PTX3. Were also compared levels of cytokine production between susceptible and resistance mice as well as PTX3$^{-/-}$ and PTX3$^{+/+}$ mice. Was found that treatment with PTX3 resulted in an increased production of all cytokines in both susceptible (BALB/c and PTX3$^{-/-}$) and resistant (C57BL6 and PTX3$^{+/+}$) mice, although to a lesser degree in the latter (FIG. 4B). Together, these data suggest that PTX3 promotes the IL-12– more than IFN-$\alpha$ dependent pathway in response to MCMV. This was also confirmed in the reactivation model in which protection by PTX3 correlated with the activation of the IL-12p70/IFN-$\gamma$-dependent pathway, particularly in condition of seropositivity of the recipients (FIG. 4C).

The Efficacy of PTX3 Depends on the IL-12p70/IFN-$\gamma$-Dependent Pathway

Figure 5:
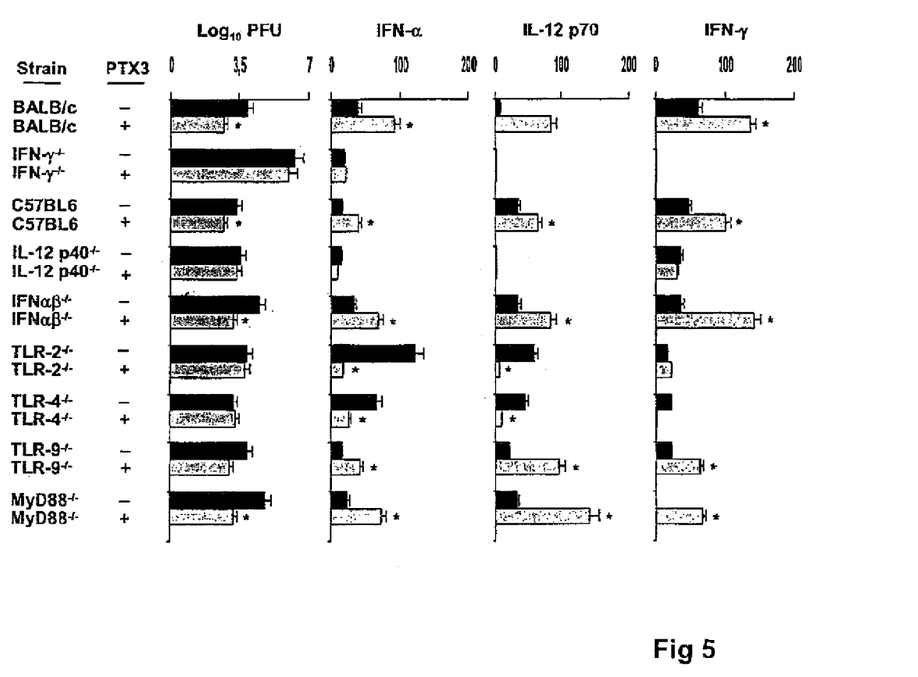

To directly evaluate the relative role of IFN-$\alpha$, IL-12p70 and IFN-$\gamma$ production in the protective efficacy of PTX3 in the acute MCMV infection, was assessed the relative efficacy of PTX3 in mice deficient for IFN-$\gamma$, IL-12 p40 and IFN-$\alpha\beta$R. As already reported (J. Exp. Med. 2003, 197:885), deficiency in IFN-$\gamma$ or IFN-$\alpha\beta$R greatly increased the susceptibility to the infection, as revealed by more than 1 log increase of the viral load in the lung as compared to the corresponding WT mice. In contrast, deficiency of IL-12 p40 did not increase significantly the viral load (from 3.4×10$^3$ to 4.2×10$^3$, WT versus IL-12 p40$^{-/-}$ mice) (FIG. 5A) PTX3 inhibited by more than 1 log the viral load in IFN-$\alpha\beta$R$^{-/-}$, an effect that was superior to that seen in WT mice. In contrast, the inhibitory activity was significantly reduced in IFN-$\gamma^{-/-}$ or IL-12p40$^{-/-}$ as compared to the corresponding WT control mice (from 6.3 to 6 log$_{10}$ in IFN-$\gamma^{-/-}$ vs 4.8 to 3.4 log$_{10}$ in BALB/c WT, and from 3.6 to 3.4 log$_{10}$ in IL-12p40$^{-/-}$ vs 3.4 to 2.9 log$_{10}$ in C57BL6 WT after PTX3 treatment) (FIG. 5A). Both IL-12 and IFN-$\gamma$ were produced at high levels in IFN-$\alpha\beta$R$^{-/-}$ mice treated with PTX3, a finding confirming the preminent role of the IL-12p70/IFN-$\gamma$ axis in the protective effect of PTX3.

PTX3 Activates the TLR9/MyD88-Independent Sensing of MCMV

Effective anti-MCMV immune surveillance required functional TLR signals, in particular the TLR9/MyD88 signaling pathway has a crucial role for a rapid MCMV clearance, whereas TLR2, TLR3, and TLR4 did not seem to play a significant role (Proc. Natl. Acad. Sci. U.S.A. 2004, 101: 3516). To assess the role of TLR in the efficacy of PTX3 in the acute infection, mice deficient for TLR signaling were challenged with MCMV and followed for viral replication in the lung. In accordance with published data (Proc. Natl. Acad. Sci. U.S.A. 2004, 101:3516), TLR9$^{-/-}$ and, particularly, MyD88$^{-/-}$ mice were more susceptible to MCMV than C57BL6 mice, while deficiency for TLR2 and TLR4 did not significantly affect mouse resistance (FIG. 5B). Not only was PTX3 still effective in TLR9$^{-/-}$ and MyD88$^{-/-}$ mice, but its efficacy was apparently increased, particularly in MyD88$^{-/-}$ mice, as compared to C57BL6 mice (from 3.4 to 2.9 log$_{10}$ in WT vs 4.8 to 3.2 log$_{10}$ in MyD88$^{-/-}$ mice and 3.9 to 3 log 10 in TLR9$^{-/-}$ mice after PTX3 treatment). Interestingly, PTX3 was completely ineffective in TLR2$^{-/-}$ and TLR4$^{-/-}$ mice, a finding suggesting the possible involvement of these TLRs in the activation of the antiviral immune response by PTX3. Here again, the efficacy of PTX3 directly correlated with levels of IL-12 and IFN-$\gamma$ that were significantly increased in supernatants of splenocytes from MyD88$^{-/-}$ and TLR9$^{-/-}$ mice, whose production was low otherwise, as already shown by others (J. Immunol. 2005, 175:6723), and ablated in TLR2$^{-/-}$ and TLR4$^{-/-}$ mice (FIG. 5). This finding is in line with published data showing that, despite a dramatic default in the serum, a delayed but significantly high level of IFN-γ can be produced in MyD88$^{-/-}$ and TLR9$^{-/-}$ mice (J. Immunol. 2005, 175:6723). Therefore, because the MyD88 adaptor is also required for the signal transduction of all other TLR, except TLR3 (Annu. Rev. Immunol. 2003, 21:335), TLR pathways, other than TLR9, are involved in the MCMV sensing and subsequent response induced by PTX3.

The present invention contemplates a therapeutic package for dispensing to, or for use in dispensing to, a patient being treated for a viral disease (or for the inhibition of the activation of the virus) comprising one or more unit doses, each unit dose comprising an amount of the long pentraxin PTX3 therein such that periodic administration of one or more of said unit doses is effective to treat, for example; HCMV; and a finished pharmaceutical container therefore, said container further containing or comprising labeling, said labeling indicating that the long pentraxin PTX3 is indicated for the treatment of patients with, for example, HCMV.

Additionally, the present invention contemplates an article of manufacture comprising packaging material and the long pentraxin PTX3 contained within said packaging material, wherein the long pentraxin PTX3 is therapeutically effective for treating HCMV, and wherein the packaging material comprises a label which indicates that the long pentraxin PTX3 can be used to treat HCMV.

In the use according to the invention, the terms "treat" or "treating" bear their usual meaning which includes preventing, prohibiting, alleviating, inhibiting, ameliorating, halting, restraining, slowing or reversing the progression, activation or reduction of the severity of a viral disease.

In the use according to the invention, the term "effective amount" refers to an amount of the compound, which is capable of performing the intended result. For example, an effective amount of the long pentraxin PTX3 that is administered in an effort to treat a viral disease is that amount which is required to prevent, prohibit, alleviate, ameliorate, halt, restrain, slow or reverse the progression, or reduce the severity of said viral disease, and the daily dose to be administered will depend, according to the judgement of the primary care physician, on the subject's weight, age and general condition of the patient.

The present invention also includes methods employing pharmaceutical formulations, which contain, as the active ingredient, the long pentraxin PTX3, in association with pharmaceutical carriers. A skilled artisan would know of such formulations and their manufacture, see, e.g., REMINGTON'S PHARMACEUTICAL SCIENCES, (16th ed. 1980).

The formulations are preferably formulated in a unit dosage form of the active ingredient. The term "unit dosage form" refers to physically discrete units suitable as unitary dosages for human subjects, each unit containing a predetermined quantity of active material calculated to produce the desired therapeutic effect, in association with a suitable pharmaceutical excipient.

The long pentraxin PTX3 can be administered in the form of a pharmaceutical composition in combination with pharmaceutically acceptable carriers or excipients, the proportion and nature of which are determined by the solubility and chemical properties of the compound in the carriers and/or excipients selected, the chosen route of administration, and standard pharmaceutical practice.

Pharmaceutical compositions are prepared in a manner well known in the pharmaceutical art see, e.g., REMINGTON'S PHARMACEUTICAL SCIENCES, (16th ed. 1980).

The carrier or excipient may be a solid, semi-solid, or liquid material, which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solution, suspensions, liposome or the like.

DISCUSSION OF THE DRAWINGS

FIG. 1

PTX3 Binds to and Inhibits Replication of CMV and Influenza Virus In Vitro (A) Binding of biotin-labelled PTX3 (PTX3bio$^+$) to human (HCMV) or murine (MCMV) virus. Different concentrations of unbiotinilated PTX3 (PTX3bio$^-$) were added for 2 hours at 37° C. to HCMV Ag-coated or MCMV-coated plates followed by the addition of different concentrations PTX3bio$^+$ for additional 2 hours at 37° C. The optical density at 450 nm was read using the Horseradish Peroxidase Substrate Kit. *P<0.05, 1 or 0.5 μg/mL vs 5 μg/mL PTX3bio$^+$; **P<0.05, PTX3bio$^+$ with and without PTX3bio$^-$. Bars indicate the standard errors. For inhibition of viral replication, MEF cells were untreated and infected with untreated MCMV (0), untreated and infected with MCMV pre-treated with 5-0.5 μg/mL PTX3 (V) or pre-incubated with 5-0.5 μg/mL PTX3 (C) and then added of untreated MCMV.−, uninfected cells. MCMV gB transcripts expression was assessed by real-time PCR, 72 hours after the infection. The results shown represent 1 representative experiment out of 3 independent experiments. (B) Binding of PTX3bio$^+$ to human H3N2 influenza virus. H3N2-coated plates were added of PTX3bio-followed by PTX3bio$^+$ as above. *P<0.05, PTX3bio$^+$ with and without PTX3bio$^-$. Bars indicate the standard errors. For inhibition of viral replication, MDCK cells were infected with H3N2 pre-treated with 0.5-5 μg/mL PTX3 and viral replication assessed by standard plaque assay. The results shown represent 1 representative experiment out of 3 independent experiments. (C) DC were generated from bone marrow progenitors of BALB/c mice in the presence of GM-CSF (CD11$^+$DC) or Flt3L (plasmacytoid, pDC), infected with MCMV (indicated as MCMV) and assessed, 48 hours later, for morphology by light microscopy and viral replication by real-time PCR as above. Cells were exposed to 5 μg/mL PTX3 for 2 hours at 37° C. before infection (indicated as PTX3+MCMV$^a$) or to PTX3-treated virions (indicated as PTX3+MCMV$^b$).−, uninfected cells.

FIG. 2

PTX3 Protects from CMV Infection and Reactivation In Vivo (A and B) Animals were infected intraperitoneally with 10$^5$ (BALB/c), 5×10$^5$ (C57BL6, PTX3$^{+/+}$ and PTX3$^{-/-}$) PFU of MCMV. Virus titers were quantified on MEF cells by standard plaque assay on tissues removed at different times. PTX3 and GCV were administered beginning the day of the infection. Controls received the diluent alone. Viral titers are expressed as log$_{10}$ (mean±standard errors, SE). Results are representative of 4 independent experiments. (C) Histological analysis of Periodic acid-Schiff-stained lung sections from PTX3$^{+/+}$ and PTX3$^{-/-}$ mice infected with MCMV and treated with PTX3 (+) as above or the diluent (−) for a week. Cellular recruitment associated with signs of parenchimal destruction, peribrochial fibrosis and Globet cell hyperplasia (magnified ×20 in the insets) were seen in PTX3$^{-/-}$ more than PTX3$^{+/+}$ mice and were ameliorated by PTX3 treatment. Hystology was done a day after treatment. Magnification ×10 in all panels. (D) BALB/c or C57BL6 mice were infected with MCMV as above. Three months later, MCMV latency was confirmed by the absence of acute MCMV infection in spleen and lung. Infected mice were used either as recipients of allogeneic donor uninfected bone marrow cells (MCMV+ recipients) or as donors of bone marrow cells (MCMV+ donors) to be injected into uninfected recipients. PTX3 (1 mg/kg/intraperitoneally) was given daily for 2 weeks, starting the day after HSCT. Dying or surviving mice (sacrificed thirty days after HSCT) were assessed for MCMV viral loads in the lungs by the plaque assay. MST, median survival time (days). Bars indicate the standard errors. *P<0.05, viral load in the lung between treated and untreated mice. (E) MCMV-infected BALB/c mice received *Aspergillus conidia* intravenously 2 weeks after the viral infection and subsequent treatment with PTX3 (1 mg/kg/intraperitoneally) daily for a week. Quantification of fungal growth was done 3 days after infection by the chitin assay and results are expressed as chitin content (micrograms of glucosamine/organ). Bars indicate the standard errors. *P<0.05, fungal load MCMV-infected vs uninfected mice. **P<0.05, fungal load in PTX3-treated vs untreated MCMV-infected mice.

FIG. 3

PTX3 Supports Dendritic Cell and NK Cell Activation In Vivo

Phenotypic analysis of total spleen and lung cells (A, C), spleen DC (B), spleen and lung NK cells (D) from MCMV-infected BALB/c mice untreated (−) or a day after a week of treatment (+) with PTX3 (1 mg/kg/intraperitoneally). None, uninfected mice. Numbers refer to the percentage of positive cells on FACS analysis. (E) Cytotoxic activity (by standard $^{51}$Cr release assay against YAC-1 targets) and frequency of IFN-γ-producing splenic NK cells by ELISPOT assay from BALB/c mice infected and treated as above. Bars indicate the standard errors. *P<0.05, Infected vs uninfected mice. **P<0.05, PTX3-treated vs untreated infected mice. The results shown represent 3 representative experiments of 5 independent experiments.

FIG. 4

PTX3 Promotes Cytokine Production (A) DC were generated from bone marrow progenitors of BALB/c mice in the presence of GM-CSF (CD11c+) or Flt3L (pDC). For cytokine production DC were pre-exposed to 5 μg/mL PTX3 before infection (a) or were untrated and infected with PTX3-treated virus (b). Cytokines were determined in culture supernatants by ELISA assay and are expressed as pg/mL. Bars indicate the standard errors. *P<0.05, cytokine production in MCMV-infected DC vs uninfected DC. **P<0.05, DC infected with PTX3-treated virus vs PTX3-treated DC. (B) Cytokine production in mice during MCMV infection. Cytokine levels (as pg/mL) in culture supernatants from spleen cells from mice with primary MCMV infection and treated with PTX3. *P<0.05, PTX3 treated vs untreated mice. (C) Cytokine production in MCMV reactivation model. BALB/c or C57BL6 mice were infected with MCMV. Infected mice were used either as recipients of allogeneic donor uninfected bone marrow cells (MCMV+ recipients) or as donors of bone marrow cells (MCMV+ donors) to be injected into uninfected recipients. PTX3 (1 mg/kg/intraperitoneally) was given daily for 2 weeks, starting the day after HSCT. Cytokine (pg/mL) levels in culture supernatants of spleen cells were determined by ELISA assay. Bars indicate the standard errors. *P<0.05, PTX3 treated vs untreated mice.

FIG. 5

PTX3 Activity is IL-12/IFN-γ-Dependent and TLR9/MyD88-Independent (A) Infection and viral load of BALB/c, IFN-γ$^{-/-}$, C57BL6, IL 12p40$^{-/-}$ and IFN-αβ$^{-/-}$ mice upon MCMV infection and PTX3 treatment. Animals were infected intraperitoneally with $10^5$ (BALB/c, IFN-γ$^{-/-}$), 5×$10^5$ (C57BL6, IL-12p40$^{-/-}$ and IFN-αβ$^{-/-}$) PFU of MCMV. Virus titers were quantified on MEF cells by standard plaque assay on lung tissues removed at 7 days after infection. PTX3 (1 mg/kg/intraperitoneally) was administered beginning the day of the infection daily for a week. Controls received the diluent alone. Viral titers are expressed as $\log_{10}$. Bars indicate the standard errors. *P<0.05, MCMV treated mice vs MCMV untreated mice. Results are representative of 4 independent experiments.

(B) MCMV replication in C57BL6, TLR2$^{-/-}$, TLR4$^{-/-}$, TLR9$^{-/-}$ and MyD88$^{-/-}$ mice treated with PTX3. Mice were inoculated intraperitoneally with 5×$10^5$ (C57BL6, TLR2$^{-/-}$, TLR4$^{-/-}$, TLR9$^{-/-}$, MyD88$^{-/-}$) PFU of MCMV and PTX3 treated as above. Lung MCMV titers were determined by plaque assay 1 week after infection. Controls received the diluent alone. Viral titers are expressed as $\log_{10}$. Bars indicate the standard errors. *P<0.05, MCMV treated mice vs MCMV untreated mice. Results are representative of 4 independent experiments.

The invention claimed is:

1. A method for inhibiting reactivation of a latent human cytomegalovirus (HCMV) infection, said method comprising:

selecting a patient having a latent HCMV infection; and administering an effective amount of long pentraxin 3 (PTX3) to said patient thereby inhibiting or reducing development of a clinical symptom caused by the reactivation of said HCMV latent infection, wherein the PTX3 is a recombinant glycosylated PTX3 expressed in mammalian cells.

2. The method of claim 1, wherein the clinical symptom is HCMV mononucleosis or an immunocompromised condition.

* * * * *